United States Patent [19]

Hare

[11] Patent Number: 5,485,229
[45] Date of Patent: Jan. 16, 1996

[54] METHOD AND APPARATUS FOR DETERMINING ELECTRICAL ACTIVITY IN THE RETINAL NERVE FIBER LAYER USING INTRINSIC BIREFRINGENT PROPERTIES OF RETINAL GANGLION CELL AXONS

[75] Inventor: William A. Hare, Tustin, Calif.

[73] Assignee: Allergan, Inc., Irvine, Calif.

[21] Appl. No.: 248,356

[22] Filed: May 24, 1994

[51] Int. Cl.$^6$ ...................................................... A61B 3/10
[52] U.S. Cl. ........................... 351/215; 351/205; 351/246
[58] Field of Search ...................................... 351/206, 215, 351/209, 210, 211, 221, 247, 246, 205

[56] References Cited

PUBLICATIONS

Tasaki, et al. Changes in Fluorescence . . . Proc Natl Acad Sci vol. 61 pp. 831–888 (1968).
Cohen et al. Light Scattering and Birefringence . . . Nature vol. 218 pp. 438–441 (1968).
Hill et al. Opacity Changes in Stimulated . . . J. Physiol vol. 108 pp. 278–281 (1949).
Hill, The Effect of Stimulation On . . . J Physiol vol. 111 pp. 283–303 (1950).
Schmitt, Morphology in Muscle and Nerve . . . unknown text pp. 68–77 (1950).
Bryant et al. Changes in Light Scattering . . . J. Cellular Comp Physiol vol. 40 (1952).
Cohen et al; Changes in Axon Birefringence . . . J Physiol V211 pp. 495–515 (1970).
Cohen et al, Changes in Light Scattering . . . J Physiol V212 pp. 259–275 (1971).
Cohen et al. Analysis of the Potential . . . J Physiol V218 pp. 205–237 (1971).
Cohen et al Changes in Light Scattering . . . J Physiol V224 pp. 701–725 (1972).
Ross et al Changes in Absorption, . . . J. Membrane Biol V33 pp. 141–183 (1977).
Hemenger, Birefringence of a Medium . . . Applied Optics vol. 28 No. 18 pp. 4030–4034 (1989).
Weinreb, et al. Histopathologic Validation . . . Arch Ophthalmol vol. 108 pp. 557–560 (1990).
Stepnoski, et al. Noninvasive Detection . . . Proc Natl Acad Sci USA vol. 88 pp. 9382–9386 (1991).
Dreher, et al al Spatially Resolved . . . Applied Optics vol. 31 No. 19 pp. 3730–3735 (1992).
Cohen et al: Evidence for Structural . . . Physol Soc pp. 85–86P Nov. 10–11, 1967.

Primary Examiner—William L. Sikes
Assistant Examiner—Hung Xuan Dang
Attorney, Agent, or Firm—Walter A. Hackler

[57] ABSTRACT

Apparatus and method for measuring retinal function in discrete regions of a retina includes selecting a discrete region of a retina having ganglion cell axons extending therefrom and to an optic nerve head and directing a linearly polarized beam of light on a probe region of retinal nerve fibers proximate the optic nerve head. Thereafter the discrete region is stimulated with light. Apparatus is provided for detecting light reflected from the probe region, before, during and after stimulation for producing an electrical signal corresponding to the amount of shifted linearly polarized light as a function of time.

11 Claims, 3 Drawing Sheets

FIG. 2.
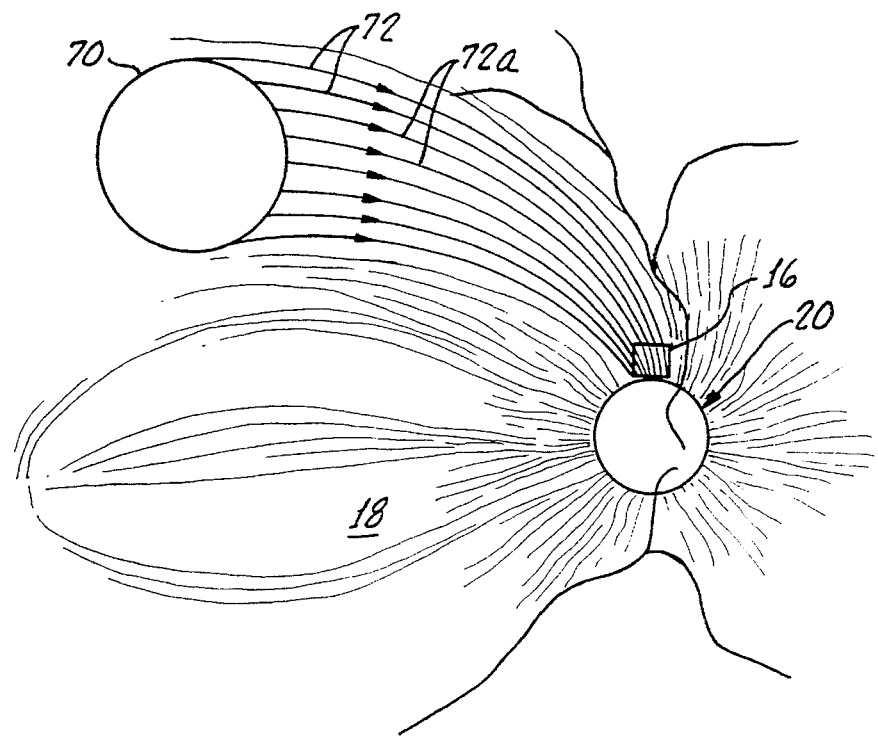
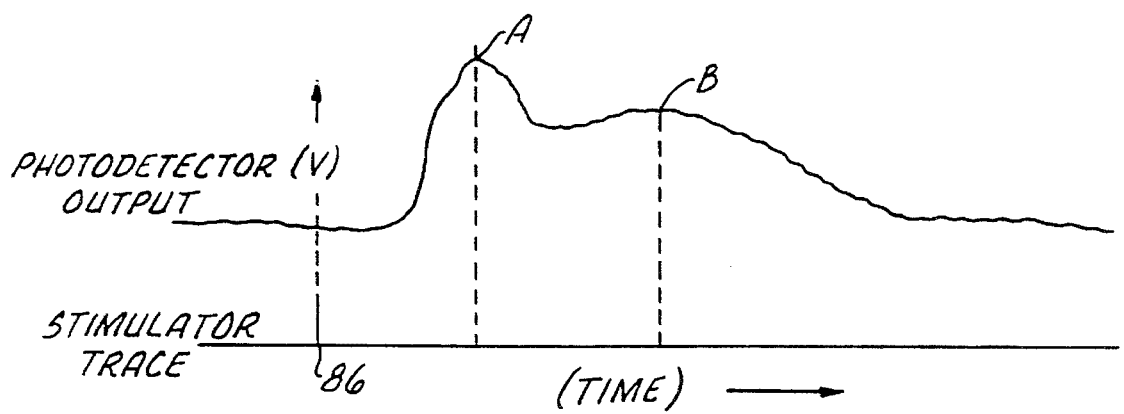
FIG. 4.

METHOD AND APPARATUS FOR DETERMINING ELECTRICAL ACTIVITY IN THE RETINAL NERVE FIBER LAYER USING INTRINSIC BIREFRINGENT PROPERTIES OF RETINAL GANGLION CELL AXONS

The present invention is directed to a method and apparatus for measuring retinal function and is more particularly directed to probing of the electrical activity in the retinal nerve fiber layer utilizing the intrinsic birefringent properties of the retinal ganglion cell axons.

In general, an object exhibits birefringent, or optically anisotropic characteristics, if its refractive index as observed in polarized light is not the same in every plane. Early work by D. K. Hill and R. D. Keynes (1949, "Opacity Changes in Stimulated Nerve," *J. Physiol.*, 108, 278–281) reported changes in the amount of light scattered by crab nerves during and after stimulation. Subsequently, D. K. Hill (1950, "Effect of Stimulation on the Opacity of a Crustacean Nerve Trunk and Its Relation to Fiber Diameter," *J. Physiol.*, 111, 283–303) proposed that the scattering of light was related to a swelling of the fibers and thereafter confirmed this phenomenon by direct measurement in Sepia axons.

Earlier work to record birefringence changes in squid axon was generally unsuccessful because of the lack of instrumental sensitivity. However, later work by L. B. Cohen, R. D. Keynes and Bertil Hille (1968, "Light Scattering and Birefringence Changes during Nerve Activity," *Nature*, 218, 438–441) confirmed changes in birefringence.

When nerves are viewed between crossed polarizers, they developed a change in intensity of transmitted light during electrical activity. Signals corresponding to this change have been found to be about ten times greater than those seen in-previous light scattering studies. In humans, early studies measured the total amount of polarization over large areas of the retina to examine birefringence.

More recently A. W. Dreher, Klaus Reiter and R. N. Weinreb (1992, "Spatially Resolved Birefringence of the Retinal Nerve Fiber Layer Assessed With a Retinal Laser Ellipsometer," *Applied Optics*, 31, 37–35) utilized instrumentation to measure polarization from changes derived from polarized light reflected from a retina.

By directing a measuring beam to various locations on the retina, the birefringence of the retina can be measured with the spatial resolution of the laser beam's focal spot size. For example, since all retinal ganglion cell axons converge to the optic nerve, measurement of the retardation along a circle around the optic nerve head can be used to describe the thickness of this layer. Using this instrumentation, it was confirmed that the retardation measured resulted from the retinal nerve fiber layer and not from the remainder of the retina.

In the course of this investigation, it was found that because of the relatively long wavelength of the HeNe laser used, scattering in the anterior layers of the retina (i.e., the nerve fiber layer) is greatly reduced, and the incident light is multireflected and/or scattered from the deeper layers of the retina and the choroid. Therefore, the laser light double passes the retinal nerve fiber layer before emerging from the eye.

In general, the investigation of the retina can be important in the detection of glaucomatous nerve fiber damage earlier than present techniques, and it also may be used for diagnosing and monitoring other retinal neuropathies when there is a loss of retinal nerve fibers.

The importance of early detection of diseases causing retinal degeneration, such as glaucoma, cannot be overemphasized. Since up to fifty percent of the optical nerve fibers may be lost prior to detectable visual field abnormalities, very early detection is possible.

The present invention provides apparatus and a method utilizing a laser and light stimulation to measure electrical activity in ganglion cell axons of the retina as a noninvasive measure of retinal function, especially ganglion cell activity. Thus, the present invention provides a potentially invaluable clinical and research laboratory tool for measuring the retinal function in discrete regions and an objective method for mapping retinal function across the visual field.

SUMMARY OF THE INVENTION

In accordance with the present invention, a method is provided for measuring retinal function in discrete regions of a retina which includes the steps of selecting a discrete region of the retina having ganglion cell axons extending therefrom and to an optic nerve head and thereafter directing a linearly polarized beam of light on a probe region of the retinal nerve fibers proximate the optic nerve head and having the ganglion cell axons from the discrete region extending therethrough.

Thereafter, the discrete region is stimulated with light and light reflected from the probe region before, during and after stimulation is detected. The detected reflected light is analyzed after stimulation and an electrical signal(s) corresponding thereto is(are) produced as a function of time.

More particularly, the step of selecting a discrete region further comprises selecting a plurality of adjacent selected regions and thereafter performing the hereinabove recited procedure in each plurality adjacent the selected regions for combining the produced electrical signals in order to map the retina. In addition, the present invention may include the analysis of electrical signals to determine activities of nerve fiber groups having different mean conduction velocities.

In other words, the method in accordance with the present invention includes the determination of electrical activity in a retinal nerve fiber layer and a method of mapping retinal function.

Apparatus, in accordance with the present invention, suitable for performing the claimed method includes means for directing a linearly polarized beam of laser light on a probe region of retinal nerve fibers proximate an optic nerve head and light-emitting means for stimulating a region of the retina distal from the optic nerve head, said region-having ganglion cell axons extending through the probe region.

Photoelectric means are provided for detecting the intensity of the beam of laser light reflected from the probe region and emitting an electrical signal corresponding thereto. In addition, the present invention may include conventional means for analyzing the electrical signals for quantifying changes in retinal function.

In addition, the apparatus, in accordance with the present invention, enables a method for early detection of changes in retinal. Preferably, the apparatus and method in accordance with the present invention provides for early detection in retinal degeneration but is not limited thereto.

BRIEF DESCRIPTION OF THE DRAWINGS

The advantages and features of the present invention will appear from the following description when considered in conjunction with the accompanying drawings in which:

FIG. 2 is a schematic of a retinal nerve fiber layer showing an optic nerve head, a probe region, and a selected region for stimulation having ganglion cell axons extending from the selected region to the probe region;

FIG. 4 is a representation of photodetector output corresponding to the electrical activity of the nerve fibers passing through the probe area.

DETAILED DESCRIPTION

Figure 1:
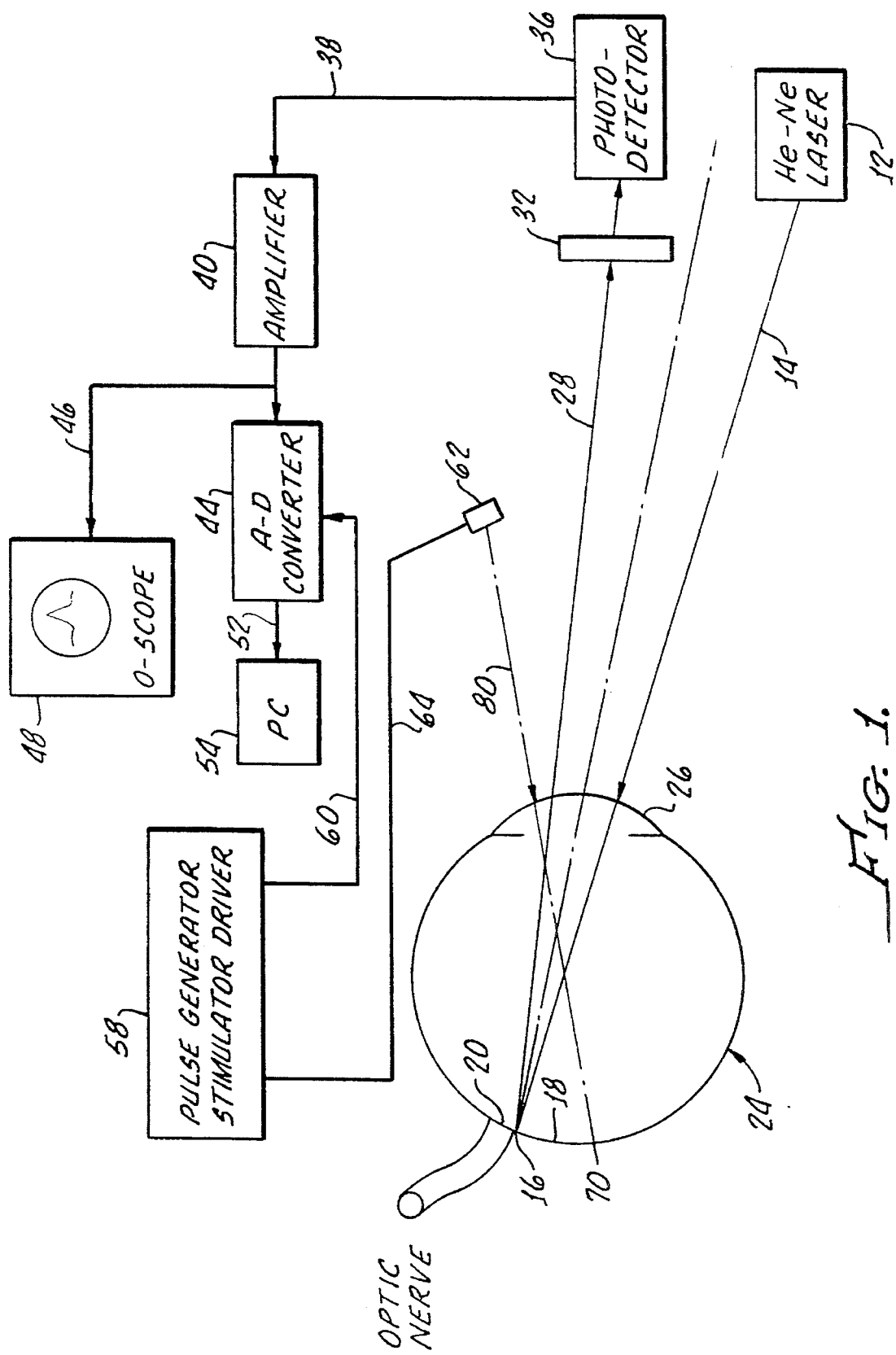
FIG. 1 is a block diagram of apparatus in accordance with the present invention suitable for performing the methods of the present invention.

Turning now to FIG. 1, there is shown apparatus 10 in accordance with the present invention, which generally includes a HeNe laser 12 incorporating optics for directing a linearly polarized beam 14 of light on a probe region 16 of retinal nerve fibers 18 proximate an optic nerve head 20 of an eye 24.

The beam 14 passing through a pupil 26 is reflected back through the pupil 26 as represented by the beam 28. An analytical polarizing filter 32 is provided for receiving the beam 28 of reflected laser light and filtering therefrom unshifted linearly polarized light and passing shifted polarized light 34 to a photodetector 36. The laser 12, filter 32 and photodetector 36 may be of any conventional design. The photodetector 36 provides a means for detecting the laser light 34 and emitting an electrical signal corresponding thereto.

The photodetector output as represented by an arrow 38 is directed to amplifier 40 which feeds amplified signal as represented by the arrow 42 into an analog to digital convertor 44 and into oscilloscope 48 as indicated by arrow 46. Output 52 from the convertor 44 may be fed into a computer 54 for analysis.

A pulse generator 58 is provided and interconnected by a line 60 to the convertor 44 and to flash lamp 62 by a line 64. The flash lamp 62 includes an optic system and provides a means for stimulating a discrete region 70 on the retina 18 having ganglion cell axons originating from the discrete region 70 and passing through the probe region 16, as shown in FIG. 2. Thus, the flash stimulation delivered to the retinal region 70 stimulates a volley of action potentials which travel along the ganglion cell axon 70 through extending through the probe region 16.

It should be appreciated that the amplifier 40, convertor 44, oscilloscope 46, computer 54, pulse generator 58 and flash lamp 62 may be of any suitable conventional design.

Figure 3:
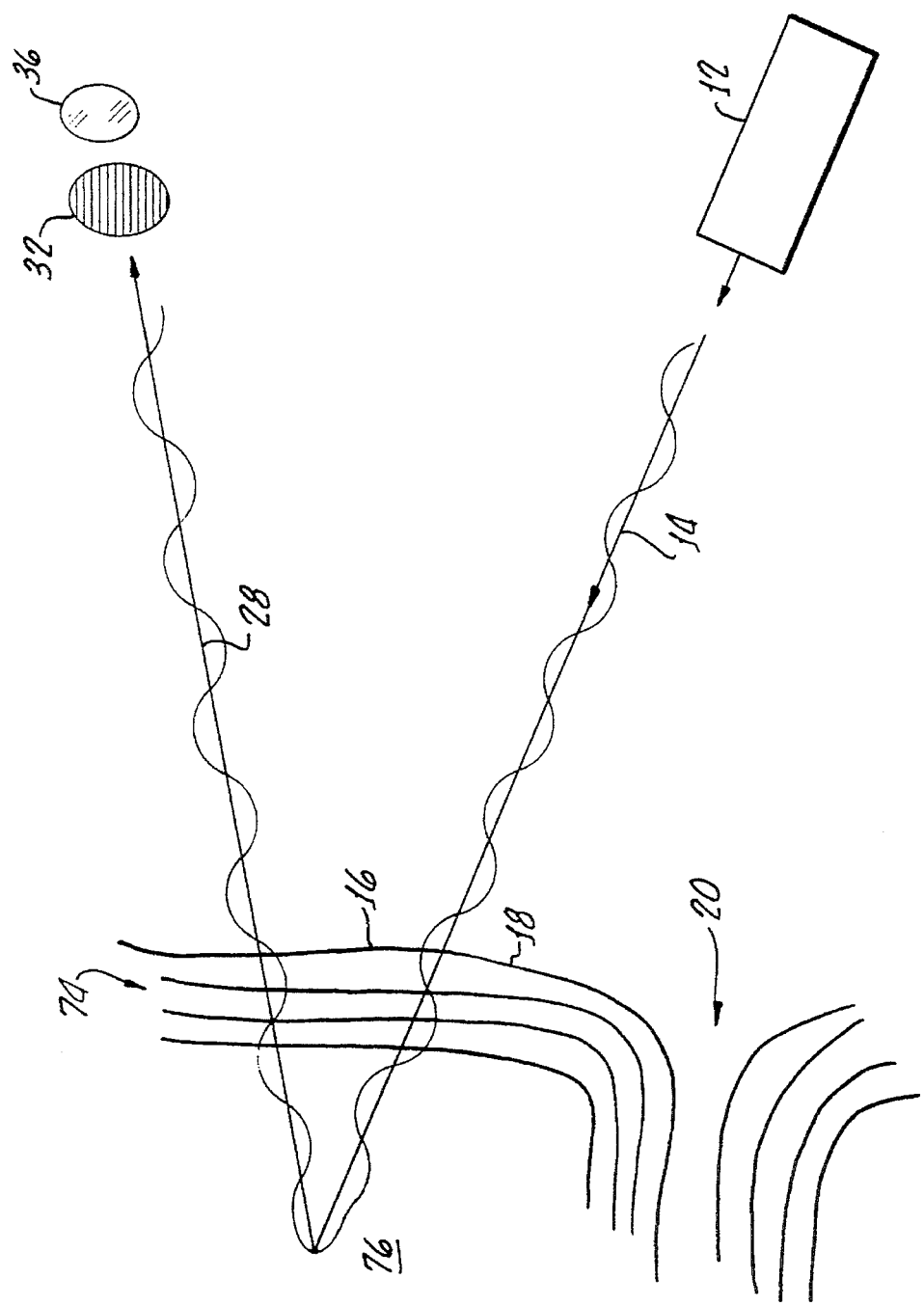
FIG. 3 is a cross-sectional illustration of the method, in accordance with the present invention, showing the reflection of the laser light focussed near the optic nerve head, being reflected from the fundus and making two passes through the peripapillary retinal nerve fibers before reception by photodetector through an analytical polarizer.

As shown in FIGS. 2 and 3, the method of the present invention includes the selection of a probe region 16 and the imaging of a highly linearly polarized laser beam 14 at the retina 18 proximate the optic nerve head 20. As shown, the incident beam 14 passes through the nerve fiber layer 74 and the electric field vector, or polarity, is rotated to a degree which is proportional to the thickness of the fiber layer 74. Light is reflected from subsurface retinal layers 76, and makes another pass through the nerve fiber layer 74 with concomitant additional rotation of the electric field vector. The reflected beam 28 is imaged at plane of the photodetector 36, which is fitted with the analytical polarizer 32.

In operation, the analytical polarizer 32 is adjusted, i.e., rotated, so that its axis is orthogonal to the polarity or orientation of the electric field vector of the incident beam. In this manner, it is adjusted to give a minimum intensity output from the detector.

Next, a light stimulus indicated by the dashed line 80 (see FIG. 1) is delivered to the selected region 70 which sends ganglion cell axons 72 through the probe region 16. The retinal stimulus provided by the light 80 excites ganglion cell activity and results in a volley of action potentials along the nerve fibers 72 passing through the probe region 16 on the way to the optic nerve head 20.

Birefringence of the axons in the probe region will shift and change the polarity of the reflected light beam 28 and the shifted polarity will be proportional to the mean level of electrical activity, i.e., greater electrical activity will result in a greater rotation of the reflected beam and more light will pass through the analytical polarizer to reach the photodetector. In this manner, the output of the photodetector is an open signal which reflects the relative change in electrical activity of the ganglion cell axons within the probe region.

Alternatively, the analytical polarizer 32 may be oriented in order that a maximum intensity output form the detector is obtained and the subsequent measurement result in a lessor output corresponding to relative changes in electrical activity of the ganglion cell axons with in the probe region.

As shown in FIG. 4, the photodetector output 84 due to a stimulation 86 represents the ensemble electrical activity of the fibers 72 passing through probe area 16. As shown, activities of fiber groups 72, 72a, (see FIG. 2) having different mean conduction velocities, can be distinguished as shown by the peaks A and B in FIG. 4. Thus, the present invention is useful for determining the activity of fiber groups having different mean conduction velocities.

In accordance with the method of the present invention, a plurality of selected regions 70 may be stimulated with a corresponding probe region 16 and, if the selected regions 70 are contiguous, a map of the entire retina 20 may be obtained.

Thus, the present invention provides a noninvasive measure of retinal function which may provide an invaluable clinical and research laboratory procedures for the assessment of retinal function, which can be used to distinguish retinal changes including but not limited to dysfunction.

Although there has been hereinabove described specific arrangements of apparatus and a method for the purpose of illustrating the manner in which the invention can be used to advantage, it should be appreciated that the invention is not limited thereto. Accordingly, any and all modifications, variations, or equivalent arrangements which may occur to those skilled in the art should be considered to be within the scope and spirit of the present invention as defined by the appended claims.

What is claimed is:

1. A method for measuring retinal function in discrete regions of a retina, said method comprising the steps of:

(a) selecting a discrete region of a retina having ganglion cell axons extending therefrom and to an optic nerve head;

(b) directing a linearly polarized beam of light on a probe region of retinal nerve fibers proximate the optic nerve head and having the ganglion cell axons from the discrete region extending therethrough;

(c) stimulating the discrete region with light;

(d) detecting light reflected from the probe region, before, during and after stimulation, unshifted linearly polarized light; and (e) analyzing a change in the detected reflected light after stimulation and producing an electrical signal corresponding thereto as a function of time.

2. The method according to claim 1 wherein the step of selecting a discrete region further comprises selecting a plurality of adjacent selected regions and thereafter performing steps (b) through (e) on each of the plurality of adjacent selected regions and combining electrical signals in order to map the retina.

3. The method according to claim 1 further comprising the step of analyzing the electrical signal to determine activities of nerve fiber groups having different mean conduction velocities.

4. A method for determining electrical activity in a retinal nerve fiber layer, said method comprising the steps of:
   (a) directing a linearly polarized beam of light on a probe region of retinal nerve fibers proximate an optic nerve head;
   (b) selecting a region of retina distal from said optic nerve head having ganglion cell with axons extending through the probe region;
   (c) stimulating the ganglion cell axons in the distal region with light;
   (d) detecting light reflected from the probe region before, during and after stimulation, unshifted linearly polarized light; and
   (e) analyzing a change in the detected reflected light after stimulation and producing an electrical signal corresponding thereto as a function of time.

5. The method according to claim 4 wherein the step of selecting a region of retina further comprises selecting a plurality of selected regions and thereafter performing steps (a) through (e) on each of the plurality of adjacent selected regions and combining electrical signals in order to map an entire retina.

6. The method according to claim 4 further comprising the step of analyzing the electrical signal to determine activities of nerve fiber groups having different mean conduction velocities.

7. A method of mapping retinal function comprising the steps of:
   (a) selecting discrete regions of a retina, each discrete region having ganglion cell axons extending therefrom, said ganglion cell axons extending through a corresponding probe region to an optic nerve head;
   (b) sequentially illuminating each of the probe regions with a linearly polarized beam of light, said probe region being proximate the optic nerve head;
   (c) stimulating each of the probe regions during laser illumination with a separate light source;
   (d) detecting light reflected from each of the probe regions;
   (e) analyzing a change in the detected reflected light after stimulation and producing electrical signals corresponding to an amount of birefringence change of the axons in the probe region; and
   (f) compiling a retinal map from the analyzed electrical signals.

8. The method according to claim 7 further comprising the step of analyzing the electrical signals to determine activity of nerve fiber groups having different mean conduction velocities.

9. Apparatus for determining electrical activity in a retinal nerve fiber layer, said apparatus comprising:
   optical means for directing a linearly polarized beam of laser light on a probe region of retinal nerve fibers proximate an optic nerve head;
   light emitting means for stimulating a region of retinal ganglion cells distal from said optic nerve head, the region having ganglion cell axons extending through the probe region;
   photoelectric means for detecting a beam of laser light reflected from said probe region and emitting an electrical signal corresponding thereto; and
   polarizer means for filtering the beam of reflected laser light and passing filtered light to said photoelectric means.

10. The apparatus according to claim 9 further comprising means for analyzing the electric signals for determination of retinal function.

11. A method for determining a change in retinal function, said method comprising the steps of:
   (a) selecting a discrete region of a retina having ganglion cell axons extending therethrough and to an optic nerve head;
   (b) directing a linearly polarized beam of light on a probe region of retinal nerve fibers proximate the optic nerve head and having the ganglion cell axons from the discrete region extending therethrough;
   (c) stimulating the discrete region with light;
   (d) detecting light reflected from the probe region, before, during and after stimulation, unshifted linearly polarized light; and
   (e) receiving shifted linearly polarized light after stimulation and producing an electrical signal corresponding to the amount of shifted linearly polarized light as a function of time.

* * * * *